US006391619B1

(12) United States Patent
Cheung

(10) Patent No.: US 6,391,619 B1
(45) Date of Patent: May 21, 2002

(54) METHODS AND COMPOSITIONS FOR SUPPRESSING GROWTH OF ALGAE

(75) Inventor: Ling Yuk Cheung, Hong Kong (HK)

(73) Assignee: Ultra Biotech Limited (GB)

( * ) Notice: Subject to any disclaimer, the term of this patent is extended or adjusted under 35 U.S.C. 154(b) by 0 days.

(21) Appl. No.: 09/797,437

(22) Filed: Mar. 1, 2001

(51) Int. Cl.[7] ............................ C12N 1/14; C12N 13/00
(52) U.S. Cl. ............................ 435/255.1; 435/254.1; 435/173.1; 435/173.8; 435/254.21
(58) Field of Search .................. 435/254.21, 173.1, 435/173.8, 254.1, 255.1

(56) References Cited

U.S. PATENT DOCUMENTS

| | | | | |
|---|---|---|---|---|
| 4,081,367 | A | 3/1978 | Hulls et al. ............... | 210/610 |
| 4,183,807 | A | 1/1980 | Yoshizawa et al. ........ | 210/611 |
| 4,211,645 | A | 7/1980 | Zajic et al. ............... | 210/611 |
| 4,559,305 | A | 12/1985 | Zajic et al. ............... | 435/243 |
| 4,816,158 | A | 3/1989 | Shimura et al. ........... | 210/610 |
| 5,075,008 | A | 12/1991 | Chigusa et al. ........... | 210/610 |
| 5,106,594 | A | 4/1992 | Held et al. ................ | 422/292 |
| 5,416,010 | A | 5/1995 | Langenberg et al. ...... | 435/468 |
| 5,476,787 | A | 12/1995 | Yokoyama et al. ....... | 435/262.5 |
| 5,567,314 | A | 10/1996 | Chigusa et al. ........... | 210/150 |
| 5,578,486 | A | 11/1996 | Zhang ....................... | 435/243 |
| 5,707,524 | A | 1/1998 | Potter ....................... | 210/606 |
| 5,879,928 | A | 3/1999 | Dale et al. ................ | 435/264 |
| 6,036,854 | A | 3/2000 | Potter ....................... | 210/177 |

FOREIGN PATENT DOCUMENTS

| | | |
|---|---|---|
| CN | 1110317 A | 10/1995 |
| EP | 0041373 | 12/1981 |
| RU | 415983 A | 11/1974 |
| WO | WO 99/60142 | 11/1999 |

OTHER PUBLICATIONS

Saccharomyces Cerevisia Meyen ex Hansen (htpp://www.i-m.ac.cn/database/yeast/y122.htm) and (http://www.i-m.ac.cn/database/catalogs.shtml) Apr. 24, 1996.*

K. Asami et al., "Real–Time Monitoring of Yeast Cell Division by Dielectric Spectroscopy", *Biophysical Journal*, 76, pp. 3345–3348 (1999).

E.K. Balcer–Kubiczek et al., "Expression Analysis of Human HL60 Cells Exposed to 60 Hz Square–or–Sine–Wave Magnetic Fields", *Radiation Research*, 153, pp. 670–678 (2000).

C.A.L. Basset et al., "Beneficial Effects of Electromagnetic Fields", *Journal of Cellular Biochemistry*, 51, pp. 387–393 (1993).

P. Conti et al., "Effect of Electromagnetic Fields on Several CD Markers and Transcription and Expression of CD4", *Immunobiology*, 201, pp. 36–48 (1999).

A.M. Gonzalez et al., "Effects of an Electric Field of Sinusoidal Waves on the Amino Acid Biosynthesis by Azotobacter", *Z. Naturforsch*, 35, pp. 258–261 (1980).

E.M. Goodman et al., "Effects of Electromagnetic Fields on Molecules and Cells", *International Review of Cytology*, 158, pp. 279–339 (1995).

T. Grospietsch et al., "Stimulating Effects of Modulated 150 MHz Electromagnetic Fields on the Growth of *Escherichia coli* in a Cavity Resonator", *Bioelectrochemistry and Bioenergetics*, 37, pp. 17–23 (1995).

W. Grundler et al., "Nonthermal Effects of Millimeter Microwaves on Yeast Growth", *Z. Naturforsch*, 33, pp. 15–22 (1978).

W. Grundler et al., "Mechanisms of Electromagnetic Interaction with Cellular Systems", *Naturwissenschaften*, 79, pp. 551–559 (1992).

O.I. Ivaschuk et al., "Exposure of Nerve Growth Factor––Treated PC12 Rat Pheochromocytoma Cells to a Modulated Radiofrequency Field at 836.55 MHz: Effects on c–jun and c–fos Expression", *Bioelectromagnetics*, 18, pp. 223–229 (1997).

F. Jelinek et al., "Microelectronic Sensors for Measurement of Electromagnetic Fields of Living Cells and Experimental Results", *Bioelectrochemistry and Bioenergetics*, 48, pp. 261–266 (1999).

A. Lacy–Hulbert et al., "Biological Responses to Electromagnetic Fields", *FASEB Journal*, 12, pp. 395–420 (1998).

C.R. Libertin et al., "Effects of Gamma Rays, Ultraviolet Radiation, Sunlight, Microwaves and Electromagnetic Fields on Gene Expression Mediated By Human Immunodeficiency Virus Promoter", *Radiation Research*, 140, pp. 91–96 (1994).

H. Lin et al., "Specific Region of the c–myc Promoter Is Responsive to Electric and Magnetic Fields", *Journal of Cellular Biochemistry*, 54, pp. 281–288 (1994).

H. Lin et al., "Magnetic Field Activation of Protein–DNA Binding", *Journal of Cellular Biochemistry*, 70, pp. 297–303 (1998).

L.I. Loberg et al., "Expression of Cancer–Related Genes in Human Cells Exposed to 60 Hz Magnetic Fields", *Radiation Research*, 153, pp. 679–684 (2000).

R.L. Moore, "Biological Effects of Magnetic Fields: Studies with Microorganisms", *Canadian Journal of Microbiology*, 25, pp. 1145–1151 (1979).

C.A. Morehouse et al., "Exposure of Daudi Cells to Low–Frequency Magnetic Fields Does Not Elevate MYC Steady–State mRNA Levels", *Radiation Research*, 153, pp. 663–669 (2000).

(List continued on next page.)

Primary Examiner—Christopher R. Tate
Assistant Examiner—Randall Winston
(74) Attorney, Agent, or Firm—Fish & Neave; James F. Haley, Jr.; Z. Ying Li

(57) ABSTRACT

Compositions comprising a plurality of yeast cells, wherein said plurality of yeast cells have been cultured in the presence of an alternating electric field having a specific frequency and a specific field strength for a period of time sufficient to substantially increase the capability of said plurality of yeast cells to suppress the growth of algae or decompose debris of algae. Also included are methods of making such compositions.

16 Claims, 1 Drawing Sheet

OTHER PUBLICATIONS

V. Norris et al., "Do Bacteria Sing? Sonic Intercellular Communication Between Bacteria May Reflect Electromagnetic Intracellular Communication Involving Coherent Collective Vibrational Modes that Could Integrate Enzyme Activities and Gene Expression", *Molecular Microbiology,* 24, pp. 879–880 (1997).

G. Novelli et al., "Study of the Effects on DNA of Electromagnetic Fields Using Clamped Homogeneous Electric Field Gel Electrophoresis", *Biomedicine & Pharmacotherapy,* 45, pp. 451–454 (1991).

J.L. Phillips, "Effects of Electromagnetic Field Exposure on Gene Transcription ", *Journal of Cellular Biochemistry,* 51, pp. 381–386 (1993).

V. Romano–Spica et al., "Ets1 Oncogene Induction by ELF–Modulated 50 MHz Radiofrequency Electromagnetic Field", *Bioelectromagnetics,* 21, pp. 8–18 (2000).

J.E. Trosko, "Human Health Consequences of Environmentally–Modulated Gene Expression: Potential Roles OF ELD–EMF Induced Epigenetic Versus Mutagenic Mechanisms of Disease", *Bioelectomagnetics,* 21, pp. 402–406 (2000).

C. Ventura et al., "Elf–pulsed Magnetic Fields Modulate Opiod Peptide Gene Expression in Myocardial Cells", *Cardiovascular Research,* 45, pp. 1045–1064 (2000).

A.M. Woodward et al., "Genetic Programming as an Analytical Tool for Non–linear Dielectric Spectroscopy", *Bioelectrochemistry and Bioenergetics,* 48, pp. 389–396 (1999).

T. Yonetani et al., "Electromagnetic Properties of Hemoproteins ", *The Journal of Biological Chemistry,* 247, pp. 2447–2455 (1972).

L. Zhang et al., "Electrostimulation of the Dehydrogenase System of Yeast by Alternating Currents", *Bioelectrochemistry and Bioenergetics,* 28, pp. 341–353 (1992).

\* cited by examiner

METHODS AND COMPOSITIONS FOR SUPPRESSING GROWTH OF ALGAE

FIELD OF THE INVENTION

The invention relates to the use of yeast cells to suppress the growth of algae and/or decompose debris of algae. These yeasts are useful in waste treatment, and are obtained by growth in electromagnetic fields with specific frequencies and field strengths.

BACKGROUND OF THE INVENTION

Environmental pollution by urban sewage and industrial waste water has posed a serious health threat to living organisms in the world. Currently, the most common methods for large-scale waste treatment, such as water treatment, include the activated sludge technology and the biomembrane technology. These technologies rely on the innate abilities of myriad natural microorganisms, such as fungi, bacteria and protozoa, to degrade pollutants. However, the compositions of these natural microbial components are difficult to control, affecting the reproducibility and quality of water treatment. Moreover, pathogenic microbes existing in these activated sludge or biomembranes cannot be selectively inhibited, and such microbes usually enter the environment with the treated water, causing "secondary pollution."

Further, most of the current technologies cannot degrade harmful chemicals such as pesticides, insecticides, and chemical fertilizers. These technologies also cannot alleviate eutrophication, another serious environmental problem around the world. Eutrophication is usually caused by sewage, industrial waste water, fertilizers and the like. It refers to waters (e.g., a lake or pond) rich in minerals and organic nutrients that promote a proliferation of plant life, especially algae, which reduces the dissolved oxygen content or otherwise deteriorates water quality. Eutrophication often results in the extinction of other organisms.

SUMMARY OF THE INVENTION

This invention is based on the discovery that certain yeast cells can be activated by electromagnetic fields having specific frequencies and field strengths to suppress the proliferation of algae and/or to decompose debris of algae. Compositions comprising these activated yeast cells can therefore be used for waste treatment, for example, treatment of sewage, industrial waste water, surface water, drinking water, sediment, soil, garbage, and manure, to reduce the growth of algae and/or to decompose debris of algae in the waste. Waste treatment methods using these compositions are more effective, efficient, and economical than the conventional methods.

This invention embraces a composition comprising a plurality of yeast cells that have been cultured in an alternating electric field having a frequency in the range of about 6340 to 6380 MHz (e.g., 6352–6370 MHz) and a field strength in the range of about 0.5 to 400 mV/cm (e.g., 70–310, 100–330, or 120–20 360 mV/cm). The yeast cells are cultured for a period of time sufficient to substantially increase the capability of said plurality of yeast cells to suppress the growth of algae. In one embodiment, the frequency and/or the field strength of the alternating electric field can be altered within the aforementioned ranges during said period of time. In other words, the yeast cells can be exposed to a series of electromagnetic fields. An exemplary period of time is about 12–450 hours (e.g., 256–432 hours).

This invention also embraces a composition comprising a plurality of yeast cells that have been cultured in an alternating electric field having a frequency in the range of about 4440 to 4470 MHz (e.g., 4452–4470 MHz) and a field strength in the range of about 0.5 to 400 mV/cm (e.g., 50–280 mV/cm). The yeast cells are cultured for a period of time sufficient to substantially increase the capability of said plurality of yeast cells to decompose algae. In one embodiment, the frequency and/or the field strength of the alternating electric field can be altered within the aforementioned ranges during said period of time. In other words, the yeast cells can be exposed to a series of electromagnetic fields. An exemplary period of time is about 12–600 hours (e.g., 320–576 hours).

Yeast cells that can be included in this composition are available from the China General Microbiological Culture Collection Center ("CGMCC"), a depository recognized under the Budapest Treaty (China Committee for Culture Collection of Microorganisms, Institute of Microbiology, Chinese Academy of Sciences, Haidian, P.O. Box 2714, Beijing, 100080, China). Useful yeast species include, but are not limited to, *Saccharomyces cerevisiae*. For instance, the yeast cells can be of the strain *Saccharomyces cerevisiae* Hansen AS2.408, AS2.414, AS2.416, AS2.422, AS2.453, AS2.486, AS2.558, AS2.562, or IFFI1292.

This invention further embraces a composition comprising a plurality of yeast cells, wherein said plurality of yeast cells have been activated such that they have a substantially increased capability to suppress the growth of algae or decompose algae as compared to unactivated yeast cells. Included in this invention are also methods of making these compositions.

As used herein, "suppressing the growth of algae" means preventing the increase in or even reducing the proliferation rate of algae. "Decomposing algae" means breaking down debris of algae into harmless products. It is to be understood that in the absence of yeast cells of this invention, the number of algae will increase naturally over a period of time. Algae include, but are not limited to, green, blue, and red algae.

A "substantially increase" means an increase of more than 10 (e.g., $10^2$, $10^3$, $10^4$, $10^5$, or $10^6$) fold.

A "culture medium" refers to a medium used in a laboratory for selecting and growing a given yeast strain, or to liquid or solid waste in need of treatment.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

DETAILED DESCRIPTION OF THE INVENTION

Figure 1:
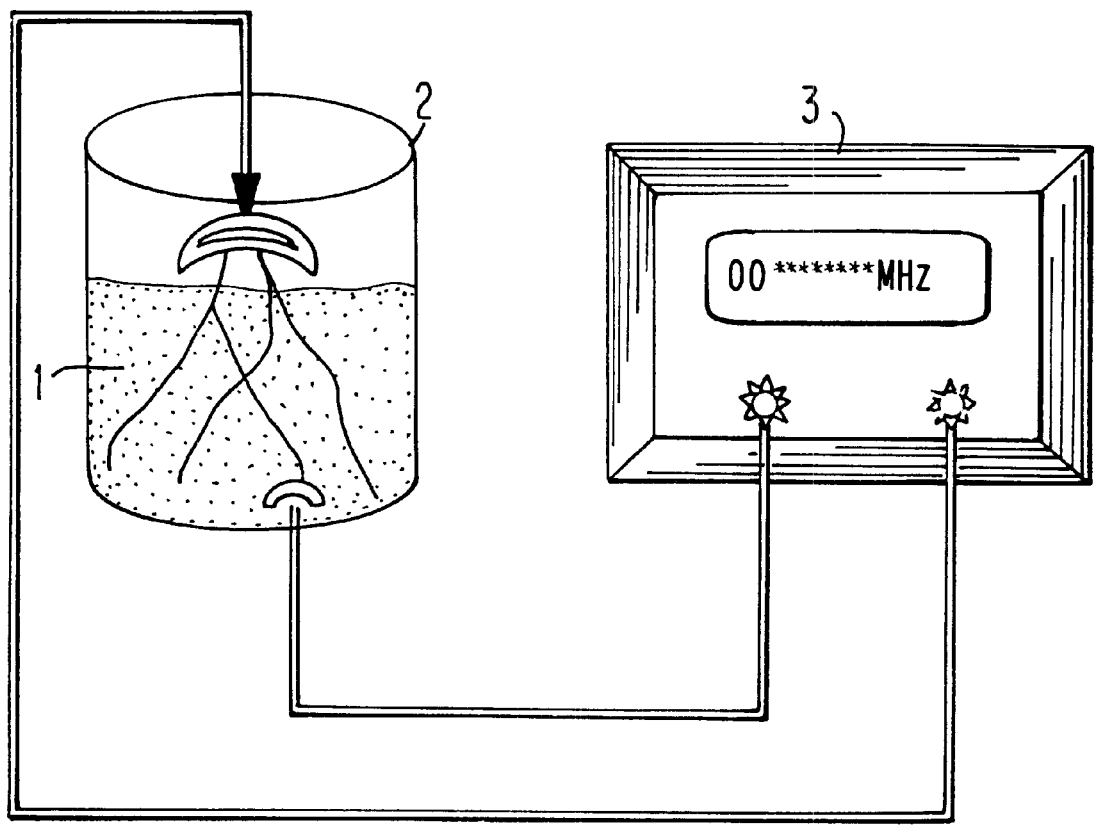
FIG. 1 is a schematic diagram showing an exemplary apparatus for activating yeast cells using electromagnetic fields. 1: yeast culture; 2: container; 3: power supply.

This invention is based on the discovery that certain yeast strains can be activated by electromagnetic fields ("EMF")

having specific frequencies and field strengths to become highly efficient in suppressing the growth of certain harmful algae or decomposing algal debris. Yeast cells having this function are defined herein as belonging to the same "functional group." Compositions containing the activated yeast cells are useful in waste treatment.

Without being bound by any theory or mechanism, the inventor believes that EMFs activate or enhance the expression of a gene or a set of genes in yeast cells such that the yeast cells become active or more efficient in performing certain metabolic activities which lead to the desired algae-suppressing and/or-decomposing result. These yeast cells are believed to create an environment that is unfavorable for the proliferation of algae.

I. YEAST STRAINS USEFUL IN THE INVENTION

The types of yeasts useful in this invention include, but are not limited to, yeasts of the genera of Saccharomyces, Schizosaccharomyces, Sporobolomyces, Torulopsis, Trichosporon, Wickerhamia, Ashbya, Blastomyces, Candida, Citeromyces, Crebrothecium, Cryptococcus, Debaryomyces, Endomycopsis, Eremothecium, Geotrichum, Hansenula, Kloeckera, Lipomyces, Pichia, Rhodosporidium, and Rhodotorula.

Exemplary species within the above-listed genera include, but are not limited to, Saccharomyces cerevisiae, Saccharomyces bailii, Saccharomyces carlsbergensis, Saccharomyces chevalieri, Saccharomyces delbrueckii, Saccharomyces exiguus, Saccharomyces fermentati, Saccharomyces logos, Saccharomyces mellis, Saccharomyces microellipsoides, Saccharomyces oviformis, Saccharomyces rosei, Saccharomyces rouxii, Saccharomyces sake, Saccharomyces uvarum, Saccharomyces willianus, Saccharomyces sp., Saccharomyces ludwigii, Saccharomyces sinenses, Saccharomyces bailii, Saccharomyces carlsbergensis, Schizosaccharomyces octosporus, Schizosaccharomyces pombe, Sporobolomyces roseus, Sporobolomyces salmonicolor, Torulopsis candida, Torulopsisfamta, Torulopsis globosa, Torulopsis inconspicua, Trichosporon behrendoo, Trichosporon capitatum, Trichosporon cutaneum, Wickerhamia fluoresens, Ashbya gossypii, Blastomyces dermatitidis, Candida albicans, Candida arborea, Candida guilliermondii, Candida krusei, Candida lambica, Candida lipolytica, Candida parakrusei, Candida parapsilosis, Candida pseudotropicalis, Candida pulcherrima, Candida robusta, Candida rugousa, Candida tropicalis, Candida utilis, Citeromyces matritensis, Crebrothecium ashbyii, Cryptococcus laurentii, Cryptococcus neoformans, Debaryomyces hansenii, Debaryomyces kloeckeri, Debaryomyces sp., Endomycopsis fibuligera, Eremothecium ashbyii, Geotrichum candidum, Geotrichum ludwigii, Geotrichum robustum, Geotrichum suaveolens, Hansenula anomala, Hansenula arabitolgens, Hansenula jadinii, Hansenula saturnus, Hansenula schneggii, Hansenula subpelliculosa, Kloeckera apiculata, Lipomyces starkeyi, Pichia farinosa, Pichia membranaefaciens, Rhodosporidium toruloides, Rhodotorula aurantiaca, Rhodotorula glutinis, Rhodotorula minuta, Rhodotorula rubar, and Rhodotorula sinesis.

Yeast strains useful for this invention can be obtained from laboratory cultures, or from publically accessible culture depositories, such as CGMCC and the American Type Culture Collection, 10801 University Boulevard, Manassas, Va. 20110–2209. Non-limiting examples of useful strains (with accession numbers of CGMCC) are Saccharomyces cerevisiae Hansen AS2.408, AS2.414, AS2.416, AS2.422, AS2.453, AS2.486, AS2.558, AS2.562, and IFFI1292.

Although it is preferred, the preparation of the yeast compositions of this invention is not limited to starting with a pure strain of yeast. A yeast composition of the invention may be produced by culturing a mixture of yeast cells of different species or strains that have the same algae-suppressing or decomposing function. The ability of any species or strain of yeasts to perform this function can be readily tested by methods known in the art.

Certain yeast species that can be activated according to the present invention are known to be pathogenic to human and/or other living organisms. These yeast species include, for example, Ashbya gossypii, Blastomyces dermatitidis, Candida albicans, Candida parakrusei, Candida tropicalis, Citeromyces matritensis, Crebrothecium ashbyii, Cryptococcus laurentii, Cryptococcus neoformans, Debaryomyces hansenii, Debaryomyces kloeckeri, Debaryomyces sp., and Endomycopsis fibuligera. Under certain circumstances, it may be less preferable to use such pathogenic yeasts in this invention. If use of these species is necessary, caution should be exercised to minimize the leak of the yeast cells into the final treatment product that enters the environment.

II. APPLICATION OF ELECTROMAGNETIC FIELDS

An electromagnetic field useful in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag-AgCl electrodes in solutions rich in chloride ions, and run at as low a voltage as possible. For general review, see Goodman et al., *Effects of EMF on Molecules and Cells*, International Review of Cytology, A Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from about 10 to 10,000 MHz, e.g., from about 6340 MHz to 6380 MHz (e.g., 6352–6370 MHz). Exemplary frequencies are 6352, 6353, 6354, 6355, 6356, 6357, 6358, 6359, 6360, 6361, 6362, 6363, 6364, 6365, 6366, 6367, 6368, 6369, and 6370 MHz. The field strength of the electric field useful in this invention ranges from about 0.5 to 400 mV/cm, e.g., from about 60 to 380 mV/cm (e.g., 70 to 310, 100 to 330, or 120 to 360 mV/cm). Exemplary field strengths are 85, 112, 136, 250, 290, and 337 mV/cm.

In another embodiment, the frequencies of EMFs useful in this invention range from about 4440 to 4470 MHz (e.g., 4452–4470 MHz). Exemplary frequencies are 4452, 4453, 4454, 4455, 4456, 4457, 4458, 4459, 4460, 4461, 4462, 4463, 4464, 4465, 4466, 4467, 4468, 4469, and 4470 MHz. The field strength of the electric field useful in this invention ranges from about 0.5 to 400 mV/cm, e.g., from about 50 to 280 mV/cm. Exemplary field strengths are 127 and 268 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength; or a different frequency and a different field strength. Such frequencies and field strengths are preferably within the above-described ranges. In one embodiment, an EMF at the beginning of the series has a field strength identical to or lower than that of a subsequent EMF, such that the yeast cell culture is exposed to EMFs of progressively increasing field strength. Although any practical number of EMFs can be used in a series, it may be preferred that the yeast culture be exposed to a total of 2, 3, 4, 5, 6, 7, 8, 9 or 10 EMFs in a series.

By way of example, the yeast cells can be cultured in a first series of alternating electric fields each having a frequency in the range of 6352 to 6370 M and a field strength in the range of 60 to 380 mV/cm. The yeast cells are exposed to each EMF for about 24 hours. After culturing in the first series of EMFs, the resultant yeast cells are further incubated in a second series of alternating electric fields for a total of 56 to 160 hours. It may be preferred that the frequencies in the second series of alternating electric fields are identical to those of the first series in sequence and the field strengths in the second series are increased to a higher level within the range of 60 to 380 mV/cm.

In another embodiment, the yeast cells can be cultured in a first series of alternating electric fields each having a frequency in the range of 4452 to 4470 MHz and a field strength in the range of 50 to 280 mV/cm. The yeast cells are exposed to each EMF for about 32 hours. After culturing in the first series of EMFs, the resultant yeast cells are further incubated in a second series of alternating electric fields for a total of 32 to 192 hours. It may be preferred that the frequencies in the second series of alternating electric fields are identical to those of the first series in sequence and the field strengths in the second series are increased to a higher level within the range of 50 to 280 mV/cm.

Although the yeast cells can be activated after even a few hours of culturing in the presence of an EMF, it may be preferred that the activated yeast cells be allowed to multiply and grow in the presence of the EMF(s) for a total of 256–432 hours.

FIG. 1 illustrates an exemplary apparatus for generating alternating electric fields. An electric field of a desired frequency and intensity is generated by an AC source (3) capable of generating an alternating electric field, preferably in a sinusoidal wave form, in the frequency range of 10 to 10,000 MHz. Signal generators capable of generating signals with a narrower frequency range can also be used. If desirable, a signal amplifier can also be used to increase the output. The alternating electric field can be applied to the culture by a variety of means including placing the yeast culture in close proximity to the signal emitters. In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy. The number of electrode wires used depends on the volume of the culture as well as the diameter of the wires. In a preferred embodiment, for a culture having a volume up to 5000 ml, one electrode wire having a diameter of 0.1 to 1.2 mm can be used for each 100 ml of culture. For a culture having a volume greater than 1000 L, one electrode wire having a diameter of 3 to 30 mm can be used for each 1000 L of culture.

III. CULTURE MEDIA

Culture media useful in this invention contain sources of nutrients assimilable by yeast cells. In this invention, a culture medium refers to a laboratory culture medium, or liquid or solid waste in need of treatment. Complex carbon-containing substances in a suitable form, such as carbohydrates (e.g., sucrose, glucose, fructose, dextrose, maltose, xylose, cellulose, starches, etc.) and coal, can be the carbon sources for yeast cells. The exact quantity of the carbon sources utilized in the medium can be adjusted in accordance with the other ingredients of the medium. In general, the amount of carbohydrates varies between about 0.1% and 5% by weight of the medium and preferably between about 0.1% and 2%, and most preferably about 1%. These carbon sources can be used individually or in combination. Among the inorganic salts which can be added to the culture medium are the customary salts capable of yielding sodium, potassium, calcium, phosphate, sulfate, carbonate, and like ions. Non-limiting examples of nutrient inorganic salts are $(NH_4)_2HPO_4$, $KH_2PO_4$, $K_2HPO_4$, $CaCO_3$, $MgSO_4$, NaCl, and $CaSO_4$.

IV. ELECTROMAGNETIC ACTIVATION OF YEAST CELLS

Eutrophication causes overgrowth of harmful algae, which dramatically decrease the level of dissolved oxygen in water and adversely affect the aquatic ecosystem. In addition, debris of these algae deposit on sediment, where oxygen levels are low, and thus cannot be effectively decomposed by natural microorganisms. Non-decomposed algal debris provide nutrients for further algal growth, generating a vicious cycle of algal pollution. Yeast of this invention can prevent or reduce such pollution by inhibiting the proliferation of algae and/or by decomposing algal debris. Algae of this invention include, but are not limited to, green, blue, and red algae.

To activate the innate ability of yeast cells to suppress algae growth or decompose algal debris, the yeast cells can be cultured in an appropriate medium under sterile conditions at 25° C.–30° C., e.g., 28° C., for a sufficient amount of time, e.g., 12–450 hours (for example, 256–432 hours), in an alternating electric field or a series of alternating electric fields as described above. The culturing process may preferably be conducted under conditions in which the concentration of dissolved oxygen is between 0.025 to 0.8 $mol/m^3$, preferably 0.4 $mol/m^3$. The oxygen level can be controlled by, for example, stirring and/or bubbling.

An exemplary culture medium is made by mixing 1000 ml of distilled water with 6 g of dehydrated algal debris, 0.2 g of NaCl, 0.2 g of $MgSO_4 \cdot 7H_2O$, 0.5 g of $CaCO_3 \cdot 5H_2O$, 0.2 g of $CaSO_4 \cdot 2H_2O$, and 0.5 g of $K_2HPO_4$. The dehydrated algae debris is prepared by centrifuging surface water (e.g., from a pond) containing a large amount of blue and green algae at 1000 g for 20 minutes, and placing the pellet under vacuum for 48 hours.

Subsequently, the yeast cells can be measured for their ability to suppress the growth of algae or decompose algal debris using standard methods known in the art, such as counting individual cells. In one exemplary method, surface water (from e.g., a river, pond, or lake) containing more than $10^{10}$ live blue algae cells/ml and more than $10^{10}$ live green algae cells/ml is inoculated with a dry yeast cell preparation at a concentration of 0.2–0.6 gL, and cultured for 24–72 hours at 15–42° C. The difference between the numbers of the above-mentioned live algae before and after 24–72 hours indicates the algae-suppressing or -decomposing capacity of the yeast cells.

Essentially the same protocol as described above can be used to grow activated yeast cells. To initiate the process, each 100 ml of culture medium is inoculated with yeast cells of the same functional group at a density of $10^2$–$10^5$ cells/ml, preferably $3\times10^2$–$10^4$ cell/m. The culturing process is carried out at about 20–40° C., preferably at about 25–32° C., for 48–96 hours. The process can be scaled up or down according to needs. For an industrial scale of production, seventy-five liters of a sterile culture medium are inoculated with the yeast cells. This culture medium consists of 10 L of the culture medium described above for this particular yeast functional group, 30 kg of starch, and 65 L of distilled water. At the end of the culturing process, the yeast cells may preferably reach a concentration of $2\times10^{10}$ cells/ml. The cells are recovered from the culture by various methods known in the art, and stored at about 15–20° C. The yeast should be dried within 24 hours and stored in powder form.

V. ACCLIMATIZATION OF YEAST CELLS TO WASTE ENVIRONMENT

In yet another embodiment of the invention, the yeast cells may also be cultured under certain conditions so as to acclimatize the cells to a particular type of waste. This acclimatization process results in better growth and survival of the yeasts in a particular waste environment.

To achieve this, the yeast cells of a given functional group can be mixed with waste material from a particular source at $10^6$ to $10^8$ cells (e.g., $10^7$ cells) per 1000 ml. The yeast cells are then exposed to an alternating electric field as described above. The strength of the electric field can be from about 100 to 400 mV/cm (e.g., 120 to 250 mV/cm). The culture is incubated at temperatures that cycle between about 5° C. to about 45° C. at a 5° C. increment. For example, in a typical cycle, the temperature of the culture may start at 5° C. and be kept at this temperature for about 1–2 hours, then adjusted up to 10° C. and kept at this temperature for 1–2 hours, then adjusted to 15° C. and kept at this temperature for about 1–2 hours, and so on and so forth, until the temperature reaches 45° C. Then the temperature is brought down to 40° C. and kept at this temperature for about 1–2 hours, and then to 35° C. and kept at this temperature for about 1–2 hours, and so on and so forth, until the temperature returns to 5° C. The cycles are repeated for about 48–96 hours. The resulting yeast cells are then dried and stored at 0–4° C.

VI. MANUFACTURE OF THE WASTE TREATMENT COMPOSITION

Yeast cells of this invention can be mixed with an appropriate filler, such as rock powder and coal ash at the following ratio: 600 L of yeast cell culture at $2\times10^{10}$ cells/ml and 760 kg of filler materials. The mixture is quickly dried at a 30 temperature below 65° C. for 10 minutes in a dryer, and then further dried at a temperature below 70° C. for no more than 30 minutes so that the water content is less than 7%. The dried composition is then cooled to room temperature for packaging.

These dried yeast compositions may be used to treat polluted surface water, sewage, or any other type of waste water. To treat polluted surface water, a yeast solution may be prepared by adding 1 kg of the dried yeast composition to 30 L of clean water. The yeast solution is then sprayed onto the polluted surface water at about 1–3 L of the solution per square meter of the polluted surface water. To treat sewage or any other type of waste water, a yeast solution may be prepared by adding about 1 kg of the dried yeast composition to 10–30 L of clean water. The yeast solution is incubated at 10–35° C. for 24–48 hours. The resultant yeast solution is then added to the waste water at about 3–20 L of the solution per liter of waste water.

VII. EXAMPLES

In order that this invention be more fully understood, the following examples are set forth. These examples are for the purpose of illustration only and are not to be construed as limiting the scope of the invention in any way.

Example 1

Suppression of the Growth of Green Algae

*Saccharomyces cerevisiae* Hansen AS2.408 cells were cultured in the presence of a series of alternating electric fields in the following sequence: the yeast cells were exposed to (1) an alternating electric field having a frequency of 6353 MHz and a field strength of 112 mV/cm for 24 hours; (2) then to an alternating electric field having a frequency of 6357 MHz and a field strength of 112 mV/cm for 24 hours; (3) then to an alternating electric field having a frequency of 6364 MHz and a field strength of 112 mV/cm for 24 hours; (4) then to an alternating electric field having a frequency of 6368 MHz and a field strength of 112 mV/cm for 24 hours; (5) then to an alternating electric field having a frequency of 6353 MHz and a field strength of 290 mV/cm for 56 hours; (6) then to an alternating electric field having a frequency of 6357 MHz and a field strength of 290 mV/cm for 56 hours; (7) then to an alternating electric field having a frequency of 6364 MHz and a field strength of 290 mV/cm for 24 hours; and (8) finally to an alternating electric field having a frequency of 6368 MHz and a field strength of 290 mV/cm for 24 hours.

To test the ability of the EMF-treated AS2.408 cells to suppress the growth of green algae, lake water or other surface water containing green algae was cultured under routine conditions to reconstitute a solution containing green algae at more than $1.0\times10^9$–$1.5\times10^9$ cells/ml. 0.1 ml of the EMF-treated AS2.408 cells at a concentration of $10^8$ cells/ml was added to 1 L of the green algae solution and cultured at 28–32° C. for 72 hours (solution A). One liter of the green algae solution containing the same number of non-treated yeast cells (solution B) or containing no yeast cells (solution C) were used as controls. After 72 hours of incubation, the solutions were examined using a flow cytometer. The results showed that after 72 hours of incubation, the number of live green algae in solution A decreased more than 28% relative to solution C. In contrast, the number of live green algae in solution B showed no significant change relative to solution C.

Example 2

Suppression of the Growth of Blue Algae

*Saccharomyces cerevisiae* Hansen AS2.414 cells were cultured in the presence of a series of alternating electric fields in the following sequence: the yeast cells were exposed to (1) an alternating electric field having a frequency of 6355 MHz and a field strength of 85 mV/cm for 24 hours; (2) then to an alternating electric field having a frequency of 6360 MHz and a field strength of 85 mV/cm for 24 hours; (3) then to an alternating electric field having a frequency of 6364 MHz and a field strength of 85 mV/cm for 24 hours; (4) then to an alternating electric field having a frequency of 6367 MHz and a field strength of 85 mV/cm for 24 hours; (5) then to an alternating electric field having a frequency of 6355 MHz and a field strength of 250 mV/cm for 56 hours; (6) then to an alternating electric field having a frequency of 6360 MHz and a field strength of 250 mV/cm for 56 hours; (7) then to an alternating electric field having a frequency of 6364 MHz and a field strength of 250 mV/cm for 24 hours; and (8) finally to an alternating electric field having a frequency of 6367 MHz and a field strength of 250 mV/cm for 24 hours.

To test the ability of the EMF-treated AS2.414 cells to suppress the growth of blue algae, lake water or other surface water containing blue algae was cultured under routine conditions to reconstitute a solution containing blue algae at more than $1.0 \times 10^9$–$1.5 \times 10^9$ cells/ml. 0.1 ml of the EMF-treated AS2.414 cells at a concentration of $10^8$ cells/ml was added to 1 L of the blue algae solution and. cultured at 28–32° C. for 72 hours (solution A). One liter of the blue algae solution containing the same number of non-treated yeast cells (solution B) or containing no yeast cells (solution C) were used as controls. After 72 hours of incubation, the solutions were examined using a flow cytometer. The results showed that after 72 hours of incubation, the number of live blue algae in solution A decreased more than 31% relative to solution C. In contrast, the number of live blue algae in solution B showed no significant change relative to solution C.

Example 3

Suppression of the Growth of Red Algae

*Saccharomyces cerevisiae* Hansen AS2.416 cells were cultured in the presence of a series of alternating electric fields in the following sequence: the yeast cells were exposed to (1) an alternating electric field having a frequency of 6352 MHz and a field strength of 136 mV/cm for 24 hours; (2) then to an alternating electric field having a frequency of 6359 MHz and a field strength of 136 mV/cm for 24 hours; (3) then to an alternating electric field having a frequency of 6363 MHz and a field strength of 136 mV/cm for 24 hours; (4) then to an alternating electric field having a frequency of 6370 MHz and a field strength of 136 mV/cm for 24 hours; (5) then to an alternating electric field having a frequency of 6352 MHz and a field strength of 337 mV/cm for 56 hours; (6) then to an alternating electric field having a frequency of 6359 MHz and a field strength of 337 mV/cm for 56 hours; (7) then to an alternating electric field having a frequency of 6363 MHz and a field strength of 337 mV/cm for 24 hours; and (8) finally to an alternating electric field having a frequency of 6370 MHz and a field strength of 337 mV/cm for 24 hours.

To test the ability of the EMF-treated AS2.416 cells to suppress the growth of red algae, lake water or other surface water containing red algae was cultured under routine conditions to reconstitute a solution containing red algae at more than $1.0 \times 10^9$–$1.5 \times 10^9$ cells/ml. 0.1 ml of the EMF-treated AS2.416 cells at a concentration of $10^8$ cells/ml was added to 1 L of the red algae solution and cultured at 28–32° C. for 72 hours (solution A). One liter of the red algae solution containing the same number of non-treated yeast cells (solution B) or containing no yeast cells (solution C) were used as controls. After 72 hours of incubation, the solutions were examined using a flow cytometer. The results showed that after 72 hours of incubation, the number of live red algae in solution A decreased more than 37% relative to solution C. In contrast, the number of live red algae in solution B showed no significant change relative to solution C.

Example 4

Decomposition of Algal Debris

'Saccharomyces cerevisiaeHansen AS2.422 cells were cultured in the presence of a series of alternating electric fields in the following sequence: the yeast cells were exposed to (1) an alternating electric field having a frequency of 4452 MHz and a field strength of 127 mV/cm for 32 hours; (2) then to an alternating electric field having a frequency of 4456 MHz and a field strength of 127 mV/cm for 32 hours; (3) then to an alternating electric field having a frequency of 44'MHz and a field strength of 127 mV/cm for 32 hours; (4) then to an alternating electric field having a frequency of 4464 MHz and a field strength of 127 mV/cm for 32 hours; (5) then to an alternating electric field having a frequency of 4452 MHz and a field strength of 268 mV/cm for 32 hours; (6) then to an alternating electric field having a frequency of 4456 MHz and a field strength of 268 mV/cm for 32 hours; (7) then to an alternating electric field having a frequency of 4462 MHz and a field strength of 268 mV/cm for 64 hours; and (8) finally to an alternating electric field having a frequency of 4464 MHz and a field strength of 28 mV/cm for 64 hours.

To test the ability of the EMF-treated AS2.422 cells to decompose debris of algae, lake water or other surface water containing debris of green, blue and/or red algae was cultured under routine conditions to reconstitute a solution containing debris of green, blue and/or red algae at more than $1.0 \times 10^9$–$1.5 \times 10^9$ cells/ml. 0. ml of the EMF-treated AS2.422 cells at a concentration of 108 cells/ml was added to 1 L of the algae solution and cultured at 28–32° C. for 72 hours (solution A). One liter of the algae solution containing the same number of non-treated yeast cells (solution B) or containing no yeast cells (solution C) were used as controls. After 72 hours of incubation, the solutions were examined. The results showed that after 72 hours of incubation, the number of green, blue and/or red algae in solution A decreased more than 26% relative to solution C. In contrast, the number of green, blue and/or red algae in solution B showed no significant change relative to solution C.

While a number of embodiments of this invention have been set forth, it is apparent that the basic constructions may be altered to provide other embodiments which utilize the compositions and methods of this invention.

What is claimed is:

1. A composition comprising a plurality of yeast cells, wherein said plurality of yeast cells are characterized by a substantial increase in their capability to suppress the growth of algae as a result of having been cultured in the presence of an alternating electric field having a frequency in the range of 6340 to 6380 MHz and a field strength in the range of 0.5 to 400 mV/cm, as compared to yeast cells not having been so cultured.

2. The composition of claim 1, wherein said frequency is in the range of 6352 to 6370 MHz.

3. The composition of claim 1, wherein said field strength is in the range of 60 to 380 mV/cm.

4. The composition of claim 1, wherein said yeast cells are derived from cells of the species *Saccharomyces cerevisiae*.

5. The composition of claim 1, wherein said yeast cells are derived from cells of the strain deposited at the China General Microbiological Culture Collection Center with an accession number selected from the group consisting of AS2.408, AS2.414, AS2.416, AS2.422, AS2.453, AS2.486, AS2.558, AS2.562, and IFFI 1292.

6. The composition of claim 2, wherein said algae are green algae.

7. The composition of claim 6, wherein said field strength is in the range of 100 to 330 mV/cm.

8. The composition of claim 2, wherein said algae are blue algae.

9. The composition of claim 8, wherein said field strength is in the range of 70 to 310 mV/cm.

10. The composition of claim 2, wherein said algae are red algae.

11. The composition of claim 10, wherein said field strength is in the 5 range of 120 to 3 mV/cm.

12. A composition comprising a plurality of yeast cells, wherein said plurality of yeast cells are characterized by a substantial increase in their capability to decompose debris of algae as a result of having been cultured in the presence of an alternating electric field having a frequency in the range of 4440 to 4470 MHz and a field strength in the range of 0.5 to 400 mV/cm, as compared to yeast cells not having been so cultured.

13. The composition of claim 12, wherein said algae are green, blue or red algae.

14. The composition of claim 13, wherein said frequency is in the range of 4452 to 4470 MHz and said field strength is in the range of 50 to 280 mV/cm.

15. A method of preparing a yeast composition, comprising culturing a plurality of yeast cells in the presence of an alternating electric field having a frequency in the range of 6340 to 6380 MHZ and a field strength in the range of 0.5 to 400 mV/cm, wherein said plurality of yeast cells are characterized by a substantial increase in their capability to suppress the growth of algae as a result of said culturing as compared to yeast cells not having been so cultured.

16. A method preparing a yeast composition, comprising culturing a plurality of yeast cells in the presence of an alternating electric field having a frequency in the range of 4440 to 4470 MHZ and a field strength in The range of 0.5 to 400 mV/cm, wherein said plurality of yeast cells are characterized by a substantial increase in their capability to decompose debris of algae as a result of said culturing as compared to yeast cells not having been so cultured.

* * * * *

UNITED STATES PATENT AND TRADEMARK OFFICE
CERTIFICATE OF CORRECTION

PATENT NO. : 6,391,619 B1
DATED : May 21, 2002
INVENTOR(S) : Ling Yuk Cheung

It is certified that error appears in the above-identified patent and that said Letters Patent is hereby corrected as shown below:

Column 1,
Line 59, change "120-20 360 mV/cm" to -- 120-360 mV/cm --.

Column 6,
Line 20, change "$NH_4)_2HPO_4$" to -- $(NH_4)_2HPO_4$ --.

Column 10,
Line 12, change "44'MHz" to -- 4462 MHz --.

Column 11,
Line 10, change "the 5 range of 120 to 3 mV/cm" to -- the range of 120 to 360 mV/cm --.

Signed and Sealed this

Twentieth Day of January, 2004

JON W. DUDAS
*Acting Director of the United States Patent and Trademark Office*